United States Patent [19]

Nieh et al.

[11] 4,412,926
[45] Nov. 1, 1983

[54] ALKYL NORBORNYL ETHER SULFONATES USEFUL FOR SOLUBILIZING PETROLEUM SULFONATES IN OIL FLUID BRINE SOLUTIONS

[75] Inventors: Edward C. Y. Nieh; Carter G. Naylor, both of Austin; Clifford L. Lambert, Georgetown, all of Tex.

[73] Assignee: Texaco Inc., White Plains, N.Y.

[21] Appl. No.: 372,493

[22] Filed: Apr. 28, 1982

[51] Int. Cl.³ .................... E21B 43/22; C07C 143/20
[52] U.S. Cl. .............................. 252/8.55 D; 260/503; 568/612; 568/616
[58] Field of Search ................. 260/503; 252/8.55 D, 252/353

[56] References Cited

U.S. PATENT DOCUMENTS

| | | | |
|---|---|---|---|
| 4,110,228 | 8/1978 | Tyler et al. | 252/8.55 D |
| 4,233,166 | 11/1980 | Allen | 252/8.55 D |
| 4,296,812 | 10/1981 | Kalfoglou | 252/8.55 D |

Primary Examiner—Nicky Chan
Attorney, Agent, or Firm—Jack H. Park; Walter D. Hunter; Richard A. Morgan

[57] ABSTRACT

Alkyl norbornyl ether sulfonates are prepared by reacting, for example, an allyl alcohol ethoxylate with an alkyl norbornene in the presence of an acid catalyst. The allyl ethers so obtained are subsequently sulfonated. These compounds, which exhibit a high degree of detergency, are useful for solubilizing petroleum sulfonates in oil fluid brine solutions.

8 Claims, No Drawings

ALKYL NORBORNYL ETHER SULFONATES USEFUL FOR SOLUBILIZING PETROLEUM SULFONATES IN OIL FLUID BRINE SOLUTIONS

BACKGROUND OF THE INVENTION

1. Field of the Invention

This invention relates to new alkyl norbornyl ether sulfonate compositions of matter. The invention also relates to a process for preparing the alkyl norbornyl ether sulfonates and to solutions containing such compositions. These solutions are useful for recovering petroleum in enhanced oil recovery processes.

2. Prior Art

Petroleum is normally recovered from subterranean formations in which it has accumulated by penetrating the formation with one or more wells and pumping or permitting the petroleum to flow to the surface through these wells. When this primary production is exhausted some form of supplemental or enhanced recovery process must be applied to the formation in order to extract petroleum.

Water flooding, which involves the injection of water into the subterranean, petroleum containing formation for the purpose of displacing petroleum toward the producing well, is the most economical and widely practiced supplemental recovery method. Water does not displace petroleum with high efficiency, however, since water and oil are immiscible, and also because the interfacial tension between water and oil is quite high. Persons skilled in the art of oil recovery have recognized this inherent weakness in water flooding and many additives have been described in the literature for decreasing the interfacial tension between the injected water and the formation petroleum. For example, U.S. Pat. No. 3,302,713 discloses the use of petroleum sulfonates prepared from a specific boiling range fraction of the petroleum feed stock for a surfactant in oil recovery operation. Other surfactants which have been proposed for oil recovery operations include alkylpyridinium salts, alkyl sulfates, alkylaryl sulfates, ethoxylated alkyl or alkylaryl sulfates, alkyl sulfonates, alkylaryl sulfonates and quaternary ammonium salts.

The above described surfactants are satisfactory in some formations, particularly where the salinity as well as concentration of divalent ions in the formation water is relatively low. Generally, the salinity must be less than about 1,000 parts per million and the concentration of divalent ions must be less than about 200 to about 500 parts per million in order to permit the use of the most commonly available primary anionic surfactants such as petroleum sulfonate.

Persons skilled in the art have recognized the limitation of simple anionic surfactants such as petroleum sulfonate and have described the use of certain solubilizing co-surfactants therewith. U.S. Pat. Nos. 3,811,504; 3,811,505; and 3,811,507 describe certain mixtures of alkyl or alkylaryl sulfonates and nonionic surfactants which exhibit satisfactory performance in petroleum formations having high salinity and/or hard water. U.S. Pat. No. 3,508,612 describes the use of a dual surfactant system comprising an organic sulfonate such as a petroleum sulfonate and a sulfated, ethoxylated primary or secondary alcohol, which is compatible with high salinity and/or high divalent ion containing formation waters. U.S. Pat. Nos. 3,827,497 and 3,890,239 relate to oil recovery fluids and processes which are compatible with high salinity formation waters and involve organic sulfonate and sulfonated, ethoxylated alcohol mixtures.

While the aforementioned multicomponent systems can be rendered soluble in high salinity and/or high divalent ion concentration formation waters, their use has not always been satisfactory because the ratio of the concentrations of the primary anionic surfactant and the solubilizing co-surfactant are extremely critical and vary with the salinity, divalent ion concentration, as well as with the specific surfactant composition being employed. If too little solubilizing surfactant is used, the primary anionic surfactant precipitates in the presence of the high salinity water. If too much solubilizing surfactant is used, the material is rendered so soluble in water that its effectiveness for purposes of reducing the interfacial tension between the drive water and the formation petroleum is greatly reduced. In either case, oil recovery falls off sharply. Moreover, the cost of the solubilizing co-surfactant is generally two to five times as great as the cost per pound of the primary anionic surfactant, and the use of excessive amounts of solubilizing co-surfactant renders an oil recovery process economically unattractive.

In view of the foregoing discussion, it can be appreciated that there is a substantial unfulfilled commercial need for an efficient and economical petroleum recovery method applicable to formations containing high salinity and/or high divalent ion concentration.

SUMMARY OF THE INVENTION

The alkyl norbornyl ether sulfonate of the present invention can be generically represented by the formula;

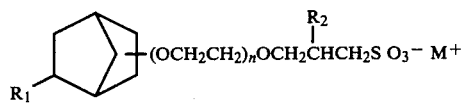

wherein $R_1$ is a substantially linear alkyl group of 4 to 12 carbon atoms; $R_2$ is selected from the group consisting of hydrogen and methyl; M is a cation selected from the group consisting of potassium, sodium and ammonium and n is an integer from 1 to 12 and preferably from 3 to 8.

The invention provides an efficient process for preparing the new products which comprises reacting an allyl alcohol ethoxylate or methyl allyl alcohol ethoxylate with an alkyl norbornene in the presence of acid catalyst.

In view of their valuable properties, particularly their detergency and solubility in brine or aqueous ionic solutions, the new ether sulfonates are particularly suited for preparation of enhanced oil recovery fluids in which it is desirable to solubilize a second surfactant in brine or aqueous ionic solution.

DESCRIPTION OF THE PREFERRED EMBODIMENTS

This invention concerns a novel ether sulfonate solubilizers which can be used in oil field brine or other hard water having polyvalent ions such as calcium and/or magnesium dissolved therein in excess of 500 parts per million. Many petroleum containing formations which contain water having calcium and/or magnesium concentrations in excess of 500 parts per million are know but cannot be exploited by means of surfactant water flooding because all surfactants previously proposed for oil recovery are insoluble or otherwise ineffective above about 500 parts per million total hardness.

It has been found that the alkyl norbornene ether sulfonates of the present invention are effective detergents and impart solubilizing characteristics to petroleum sulfonates in brine or aqueous solutions containing divalent ions in a concentration of from about 500 to about 12,000 parts per million total hardness.

The alkyl norbornyl ether sulfonate of the present invention can be generically represented by the formula:

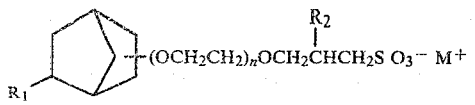

wherein $R_1$, is a substantially linear alkyl group of 4 to 12 carbon atoms; $R_2$ is selected from the group consisting of hydrogen and methyl; M is a cation selected from the group consisting of potassium, sodium and ammonium and n is an integer of from 1 to 12, and preferably from 3 to 8.

As previously pointed out $R_1$ is a substantially linear alkyl group of 4 to 12 carbon atoms. Linear alkyl groups of 4 to 12 carbon atoms are preferred for their biodegradability. However, alkyl groups that are only branched next to the double bond (beta carbon atom) and wherein the branch consists of no more than one carbon atoms, display biodegradability. Highly branched branched hydrophobes display less biodegradability and for this reason are not preferred in the present composition of matter even though their detergency and solubilizing characteristics are similar to those of the present invention.

When $R_1$ in the above formula falls below 4 carbon atoms the molecule does not display sufficient detergency for use in an enhanced oil recovery process. Molecules of greater than 12 atoms display slow detergency action and are considered inefficient for the recovery of petroleum from underground formations.

In the formula $R_2$ may be either hydrogen or a methyl group. A difference in solubility may be imparted to the molecule by selecting between hydrogen and a methyl group. Likewise M is a cation selected from potassium, sodium and ammonium. The cation is chosen for compatibility with the solution in which it resides which includes other detergents and brine salts. The sulfonate salt is then produced by the methods well known in the art (U.S. Pat. No. 4,267,123).

Sources of alkyl groups for the present invention are alpha-olefins from the Zeigler reaction and cracked wax. These sources provide alkyl groups that are substantially linear, i.e. about 80% to 90% of the alkyl groups are linear and 10% to 20% are branched such that the branch is no large than one carbon atom and occurs at the next to the double bond (beta position).

A typical solution containing the composition of the present invention will consist of alkyl norbornyl ether sulfonate molecules wherein the substantial number of molecules contain a linear $R_1$. The solution will however by the nature of alpha-olefin synthesis be a mixture containing some branched molecules wherein the branch is no longer than one carbon atom and occurs at the beta carbon in the chain. Such a mixture is within the scope of the present invention and is the essential meaning of the term "substantially linear".

The alkyl norbornyl ether sulfonates of this invention are superior detergents as they have the desirable properties of hydrolytic stability, biodegradability and effectiveness in brine media. These products have a wide range of applications including recovering petroleum in an enhanced oil recovery process where a solubilizer of petroleum sulfonates is required.

Preparation

The following equations express the reaction sequence.

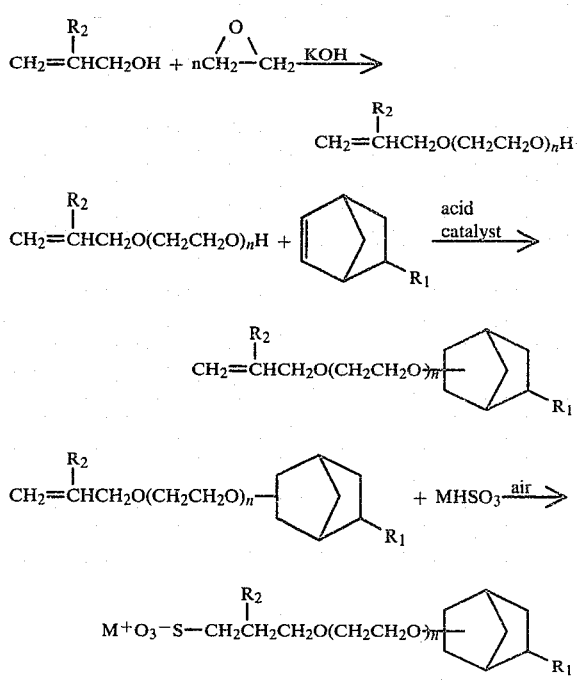

The new compositions of the present invention can be prepared by a variety of methods but are preferably prepared by condensing an alpha-olefin containing at least six carbon atoms with a conjugated diolefin such as cyclopentadiene in a Diels-Alder condensation reaction to form an alkyl-substituted norbornene, and then reacting the resulting norbornene with a polyethoxylate of allyl alcohol or methyl allyl alcohol in the presence of an acidic catalyst.

The formation of the alkyl-substituted norbornenes by reacting an alpha-olefin with a cyclopentanediene or dicyclopentadiene can be illustrated by the following equation:

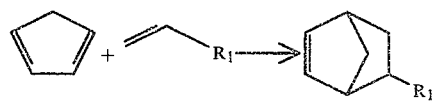

wherein $R_1$ may be a substantially linear alkyl group as described above. It is well known that the dicylopentadienes are in equilibrium with the corresponding cyclopentadienes and the use of the dicyclopentadienes, as in some of the working Examples, is in effect addition of the cyclopentadiene as shown in the above equation.

The alpha-olefins used in the preparation of the alkyl-substituted norbornenes by the reaction shown above may be of any type but are preferably the 1-alkenes containing at least six carbon atoms and not more than 15 carbon atoms. Such olefins may be exemplified by 1-hexene, 1-octene, 1-dodocene, 1-tetradecene, 1-octadecene, 1-eicosene and 3-butyloctene-1, and the like, and mixtures thereof. These olefins are preferably obtained from the Zeigler reaction and cracked wax.

The reaction between the alpha-olefin and the cyclopentadiene or dicyclopentadiene to form the alkyl-substituted norbornene as shown in above equation can be accomplished by heating the components together in a sealed autoclave at a temperature generally ranging from about 150° C. to about 300° C., and more preferably at about 220° C. The pressure may be varied as needed to keep the reagents in the liquid phase at the temperature selected which generally will be from about 1 to about 2 atmospheres. The components can be combined in a variety of different ratios varying from stoichiometric amounts up to an excess of alpha-olefin reactant. In general, it is preferred to utilize the alpha-olefin in large excess, e.g. from 2 to 6 molar excess. More specifically, molar ratios of cyclopentadiene to alpha olefin may vary from about 1:1 to about 1:5 as needed or desired. Solvents may be utilized as desired, but in many cases the excess alpha-olefin furnishes sufficient fluidity for the desired condensation reaction. The desired alkyl-substituted norbornenes can be recovered from the reaction mixture by any suitable means, such as distillation, solvent extraction and the like.

In view of the different steric arrangements that may result from this type of condensation, the resulting products will generally be a mixture of endo- and exo-derivatives as represented by the following illustration of the structure of endo-5-butyl-2-norbornene and exo-5-butyl-2-norbornene:

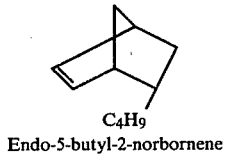
Endo-5-butyl-2-norbornene

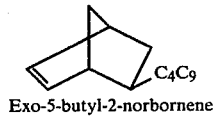
Exo-5-butyl-2-norbornene

Examples of such mixtures of steric isomers include, among others, a mixture of endo-5-octyl and exo-5-octyl-2-norbornene, a mixture of endo-5-dodecyl and 6-dodecyl-2-norbornene, a mixture of endo-5-tetradecyl and exo-5-tetradecylnorbornene-2, a mixture of endo-5-heptyl and exo-5-heptyl-2-norbornene and a mixture of endo-6-butyl and exo-6-butylnorbornene-2. These isomers have closely-related boiling points and react substantially the same in the formation of the new products of the present invention so that the isomers can be used as a mixture without further separation.

The alkyl-substituted norbornenes prepared as above are then reacted with the polyethoxylate of allyl alcohol or polyethoxylate of methyl allyl alcohol in the presence of an acidic catalyst. The reaction can be illustrated by the following equation:

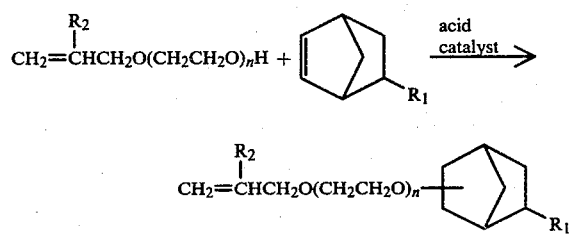

wherein $R_1$, $R_2$ and n are as described above.

The reaction is accomplished by heating the alkyl-substituted norbornene with the allyl polyethoxylate or methyl allyl polyethoxylate in the presence of an acidic catalyst. The acidic catalyst employed may be of the known Friedel-Crafts or Lewis acid type catalysts. Such catalysts include, among others boron trifluoride complexes, such as their ether complexes, hydrofluoric acid, ion-exchange resins, such as Amberlyst ® 15, a crosslinked styrene-sulfonic acid resin manufactured by the Rohm and Haas Co., and Nafion ®, a polyfluoro carbon-supported perfluoro-sulfonic acid resin manufactured by E. I. du Pont de Nemours and Co., etc., and mixtures thereof. Preferred catalysts include the boron trifluoride catalysts and particularly the complexes, such as the ether complexes as, for example, boron trifluoride diethyl ether complex, boron trifluoride cyclohexyl ether complex, and the like, and mixtures thereof. Suitable substitutes include the corresponding boron tribromide and boron triiodide complexes. The amount of the acidic catalyst employed may vary over a wide range depending upon the catalyst selected, reactants and conditions. In general, the amount of the catalyst will vary from about 0.01% to 5% by weight of reactants and more preferably from about 0.1% to 5% by weight of reactants.

The proportions of the alkyl-substituted norbornene and the allyl polyethoxylate or methyl allyl polyethoxylate to be used in the reaction may vary over a wide range. In most cases, it is desirable to utilize the components in approximately stoichiometric amounts although it is sometimes convenient to utilize an excess of either reactant. In general, the reactants are employed in molar ratios of the alkyl-substituted norbornene to the allyl polyethoxylate or methyl allyl polyethoxylate varying from about 1.5:1 to 1:1.5.

The reactants can be combined by themselves or solvents or diluents may be utilized as needed or desired. In some cases, it may be desirable to utilize a solvent, such as hydrocarbon solvent as cyclohexane or heptane alone or in combination with other inert liquids to facilitate the reaction.

The temperature employed in the reaction between the substituted norbornene and the allyl polyethoxylate or methyl allyl polyethoxylate may vary over a wide range depending upon the catalyst selected, nature of the reactants and reaction rate desired. In most cases, the temperature will vary from about 100° C. to about 200° C. and still more preferably from 100° C. to 150° C. Pressures may also vary but are preferably between about 1 and about 20 atmospheres. It is generally preferred to conduct the reaction in an inert atmosphere, such as in the presence of nitrogen.

The desired allyl alkyl-substituted norbornyl polyoxyethylene ethers of the invention can be recovered from the reaction mixture by any suitable means, such as distillation, solvent extraction, and the like. Preferably the unreacted components are removed by distillation leaving the desired product as residue.

The allyl alkyl-substituted norbornyl polyoxyethylene ether product is then sulfonated to form the alkyl norbornyl ether sulfonates of the present invention. The reaction is carried out by addition of a buffered solution containing the allyl alkyl-substituted norbornyl polyoxyethylene ether while stirring vigorously and passing a slow steam of air or oxygen through the reaction vessel. All small, water-soluble alcohols, e. g., methanol, ethanol, tertiary-butyl alcohol, propanol, isopropanol, may be used. The reaction is generally carried on under ambient conditions of temperature and pressure although higher pressures and temperatures may be used if desired. Product is recovered by conventional methods such as solvent extraction. An example of this procedure is given in Example I, Step 4.

Petroleum Sulfonate Surfactant

Petroleum sulfonates which are presently among the more popular classes surfactants being considered for supplemental oil recovery techniques are used in the solution of the present invention. The various materials available under the general name of petroleum sulfonates vary in composition according to the petroleum fraction used for sulfonation and in the degree of sulfonation imparted to the petroleum fraction. A preferable petroleum sulfonate is described in U.S. Pat. No. 3,302,713 disclosing a petroleum sulfonate prepared from a petroleum fraction whose boiling range is from 700° F. to 1100° F. which corresponds to a molecular weight range of from about 350 to about 500. The sodium salt of the sulfonation product of this petroleum fraction is an excellent material for use in the subject invention. The potassium and ammonium salts are also useful.

Mixtures of petroleum sulfonates can also be employed as the sulfonate component of this invention. For example, a mixture of a predominantly water soluble petroleum sulfonate having an average equivalent weight of less than 400 and preferably less than 350 may be utilized along with a second petroleum sulfonate which is at least partially oil soluble and preferably part oil soluble and part water soluble and having an average equivalent weight of about 400 to about 600 and preferably about 450 to about 550.

Petroleum sulfonate is a particularly desirable primary surfactant for oil recovery purposes because it is readily available, comparatively inexpensive and quite effective under certain conditions for recovering petroleum from subterranean, petroleum-containing formations. Petroleum sulfonate is, unfortunately, insoluble in water having salinities greater than about 5000 parts per million total dissolved solids, and/or more than about 500 parts per million divalent ions which are generally calcium and/or magnesium. If a normally water soluble petroleum sulfonate is added to a brine having greater salinity and/or divalent ion concentration than the above-identified limits, the petroleum sulfonate is insoluble and will precipitate and ultimately settle out of the solution, forming a layer usually under the aqueous solution. If such a fluid were injected into a subterranean, permeable oil formation, little interfacial tension reduction would be accomplished because the petroleum sulfonate is not soluble in the aqueous fluid in which it is injected; moreover, there is a considerable probability that plugging of at least some of the small capillary flow channels in the oil formation would occur. Accordingly, either a different surfactant must be utilized, which is at least slightly soluble in the formation water in which the fluid is to be injected, or another material must be added to the surfactant fluid which will have the effect of increasing the solubility of the primary anionic surfactants, e.g., petroleum sulfonate or other organic sulfonate in the presence of the salinity and divalent ion-containing formation water. Alcohols are sometimes employed for this purpose, although they have only limited effectiveness and, additionally, it is preferable to utilize a material which is itself a surface active agent and so is capable of reducing the interfacial tension between the formation petroleum and the injected drive water.

Solubility Testing

The alkyl norbornene ether sulfonate of this invention is a suitable solubilizing co-surfactant and may be combined with organic sulfonate such as petroleum sulfonate, and when a proper ratio is achieved between the concentration of the organic sulfonate and the solubilizing alkyl norbornene ether sulfonate, the organic sulfonate is rendered soluble in the presence of high salinity and/or high divalent ion-containing formation water and so can effectively reduce the interfacial tension between oil and water and thereby recover substantial amounts of oil from a formation through which the aqueous surfactant solution is passed.

The choice of solubilizing co-surfactant is influenced by the formation water salinity and divalent ion concentration and by the formation temperature. The ethoxylated alcohols and thiols are effective up to salinities of about 20,000 to 50,000 parts per million total dissolved solids and in formations whose temperatures are as high as 100°–150° F. The alkyl or alkylaryl polyethoxy sulfates are effective in higher salinities, up to 200,000 parts per million, but hydrolyze at temperatures about 150° F. The alkyl or alkylaryl polyethoxyalkyl sulfonates are tolerant of both very high salinities and high temperature.

It has been found that the degree of solubility of the surfactant composition in the field water is extremely critical to the oil recovery efficiency in the process. If the surfactant is much more soluble in water than oil, then the surfactants tends to be distributed throughout the bulk of the water phase including both formation water and injected drive water, and little effectiveness will be achieved at the interfacial zones between oil and water. Similarly, if the surfactant is substantially more soluble in oil than it is in water, the surfactant will partition into and distribute itself throughout the oil phase, and will have little effect on the surface tension existing at the interfacial zone between oil and water. The optimum surfactant effectiveness is achieved if there is a condition of borderline solubility of the surfactant fluid in the drive water and/or formation water, so the surfactants tend to exist in higher concentrations at the interfacial zone between oil and water than in either the oil phase or the water phase.

It has been found that when using blends of organic sulfonates such as petroleum sulfonates and one or more solubilizing co-surfactants such as an alkyl norbornene ether sulfonate, the optimum oil recovery efficiency occurs when the concentrations of the materials were carefully balanced so as to produce a condition of borderline solubility. If too little solubilizing co-surfactant is used in combination with the primary surfactants are rendered soluble and at least a portion thereof will precipitate in the aqueous solution. This can, as discussed above, result in at least reducing the effectiveness of the surfactant fluid for the purpose of recovering oil, and may lead to permanent, irreversible damage to permeability of the formation matrix, which will prevent any further displacement of petroleum from the formation. On the other hand, if more than the minimum amount of solubilizing co-surfactant which achieves the conditions which we have described above as borderline solubility is used in combination with primary anionic blended organic sulfonate surfactants, the surfactants are rendered too soluble in the aqueous phase and the amount of oil displaced by such a solution being injected into a formation is reduced fairly substantially. Moreover, since the cost of the solubilizing co-surfactants is generally from two to five times the cost of the primary anionic organic sulfonate surfactant, the result of using too much solubilizing co-surfactant is that the fluid cost is increased and the amount of oil recovered by the use of the fluid is decreased, with rapidly diminishing economic attractiveness of the process.

The amount of solubilizing co-surfactant necessary to achieve the above-described desired condition of borderline solubility is highly dependent on all of the possible variations in the structural characteristics of the surfactant molecules employed. The average equivalent weight of the anionic primary organic sulfonate surfactant, for example will affect the amount of solubilizing co-surfactant required to achieve the condition of borderline solubility. In the instance of using alkyl norbornene ether sulfonates as solubilizing co-surfactants, any change in the length of the alkyl chain which comprises the hydrophobe of the surfactant molecule, or a change in the number of ethylene oxide groups condensed with the molecule, will change the amount of that solubilizing co-surfactant needed to achieve the condition of borderline solubility with whatever primary anionic surfactant or mixture thereof it is used. Furthermore, the aqueous fluid salinity and the concentration of divalent ions present in the fluid will also vary the amount of the surfactants needed to achieve borderline solubility. Generally, higher salinity and/or higher concentrations of divalent ions of the aqueous fluid in which the surfactants are dissolved require increasing number of ethylene oxide units to be present on the solubilizing co-surfactant molecule.

It has been found that the only satisfactory method for determining the proper concentrations of primary anionic surfactant and solubilizing co-surfactant involves actually preparing a series of solutions containing the materials being considered for use in particular application in various concentrations, and determining the ratio of anionic primary surfactant to solubilizing co-surfactant which produces the desired condition of borderline solubility in the particular environment of salinity and hardness in which the surfactants are to be employed in a surfactant flood. It is highly desirable that the surfactant fluid salinity and concentration of divalent ions match the salinity and divalent ion concentration of the formation water as closely as possible, so the surfactants can be tailored to operate in an optimum fashion in that particular aqueous environment.

As a starting point, at least 3 and preferably at least 5 different solutions should be prepared for each blend of two or more organic sulfonates, e.g., petroleum sulfonate, samples to be tested. The total concentration of the blends should be held constant at a value of about 1% to 2% by weight and the concentration of solubilizing co-surfactant varied from about 0.1% to about 1.0% by weight. Stated another way, the total concentrations should vary between 1% and 3% by weight and the weight ratio of solubilizing co-surfactant to primary surfactant blend should be varied between 0.1 and 4.0 and preferrable less than 1.0.

Having compared the series of surfactants in the formation water as described above, the minimum ratio of solubilizing co-surfactant to each primary anionic surfactant blend which results in the desired condition of borderline solubility is determined by either of several procedures.

The samples can be mixed thoroughly and allowed to stand for at least several hours and preferably overnight. Samples containing insufficient solubilizing co-surfactant will separate into two distinct phases; a relatively clear aqueous phase and a separate surfactant-oil phase. Depending on the particular surfactants used, the salinity, and other factors, the clear phase may be on the top or bottom. The first sample in the series (i.e., the sample having the least amount of solubilizing co-surfactant) which does not exhibit two distinct phases is the sample corresponding to borderline solubility. A second or more series of such tests may be made to define the conditions of borderline solubility more precisely. In another method, the samples are placed in a suitable cell and the electrical conductivities of each of the samples are determined. The conductivity is then expressed as a function of the ratio of the concentration and preferably the function is represented graphically. In some instances a sharp minimum value will be identified; whereas in other cases the conductivity function will exhibit a clearly identified inflection point, but the sign of the slope will not necessarily change. In still other situations, an inflection point will occur first as the solubilizer concentration is increased and somewhat later a minimum value will be identified, in which case the inflection point identifies the preferred value. The ratio of surfactants which result in the minimum conductivity or in the occurrence of the first inflection point of the conductivity function, is the ratio which will produce the condition of borderline solubility in the aqueous surfactant fluid, and is also the ratio of surfactants which we have found will achieve the optimum oil recovery in a formation containing water having the salinity and hardness similar to that utilized in the tests.

It has been discovered that by preparing a number of samples of blended organic sulfonates such as petroleum sulfonates for example, which organic sulfonates have different average equivalent weights and different equivalent weight ranges and distributions and determining the amount of any preselected solubilizing co-surfactant required to reach the condition of borderline solubility for various ratios of such blended materials, it is possible to identify a preferred blend of organic sulfonates which will achieve the maximum possible oil recovery at the conditions of the test using the least amount of solubilizing co-surfactant. Since the cost of the preferred solubilizing co-surfactants is from three to five times the cost of petroleum sulfonates, the economics are highly favorable when such minimum solubilizer-containing fluids are used for a surfactant flooding oil recovery process. The most cost-effective organic sulfonates for use in forming the blend to be used in a particular application are identified by determining which blend requires the minimum amount of solubilizing co-surfactant to achieve a condition of borderline solubility in the field water to be employed in application, or in an aqueous fluid having about the same salinity and divalent ion concentration the field water to be employed in the particular application. Generally, commercially available samples in petroleum sulfonates have characteristic average equivalent weight values and ranges of equivalent weights which are relatively constant from one batch to another and which are determined by the hydrocarbon feed stocks used to prepare the petroleum sulfonates as well as by the manufacturing processes employed. There are many commercially available products from which the two or more products to blend together may be chosen. Some products are predominantly water soluble, some are predominantly oil soluble and some have varying amounts of oil soluble and water soluble components. While it is taught in the prior art to mix a water soluble and an oil soluble petroleum sulfonate to form a blend which is more effective for oil recovery purposes than either product alone, there are many possible blends of different oil soluble and water soluble petroleum sulfonates possible, some of which produce good results and some of which produce poor results in our process. Moreover, a blend of two particular sulfonates which yields excellent results in one application may produce poor results in another having significantly different formation water salinity, divalent ion concentration, etc. Finally, different blends may be found which produce equivalent oil recovery efficiencies under a particular set of test conditions but which require significantly different amounts of solubilizing co-surfactant, which causes one system to be much more costly than another.

The method of determining the optimum surfactant to solubilizing co-surfactant ratio for a given brine is found in U.S. Pat. No. 4,066,124 which is incorporated herein in its entirety by reference.

It has been found that aqueous brine solutions displaying very beneficial properties can be made using alkyl norbornyl ether sulfonates. The aqueous brine solution comprises:

(a) about 0.1 wt% to about 2 wt% of an alkyl norbornyl ether sulfonate of the formula:

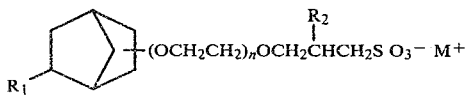

wherein $R_1$ is a substantially linear alkyl group of 4 to 12 carbon atoms; $R_2$ is selected from the group consisting of hydrogen and methyl; M is a cation selected from the group consisting of potassium, sodium and ammonium and n is an integer of from 1 to 12 and;

(b) about 0.1 wt% to about 4 wt% of a petroleum sulfonate.

Particularly beneficial properties are achieved when wherein the alkyl norbornyl ether sulfonate, n is an integer of from 3 to 8.

Once the optimum blend, total concentration of surfactants and weight ratio of solubilizing co-surfactant to blended primary surfactant are identified as described above, the field procedure is similar to field practices commonly used for surfactant flooding operations. No fresh water preflush is ordinarily needed since the surfactants are tailored to operate optimally at the salinity and divalent ion concentration of the formation water. Sacrificial agents may be used to reduce surfactant adsorption if the particular formation being exploited adsorbs the surfactants to be used.

Use In Enhanced Oil Recovery

The surfactant fluid is preferably prepared in formation water or field water having a salinity and divalent ion concentration about equal to the formation water. The quantity of surfactant fluid utilized will generally be from 0.1 to 1.0 pore volume based on the pore volume of formation to be swept by the surfactant fluid. The surfactant fluid should be followed by injection of a mobility buffer, which is an aqueous solution of a hydrophilic, viscosity increasing polymer such as polyacrylamide or polysaccharide. Generally from 50 to 1000 parts per million polymer concentration is sufficient to produce a fluid having a viscosity greater than the formation petroleum viscosity, which is adequate to ensure efficient displacement. From 0.1 to 0.5 pore volumes of the viscous mobility buffer solution is used. This is in turn followed by injection of field water to displace all of the injected fluids and petroleum through the formation to the production well. Field water injection is continued until the oil cut of the produced fluid drops to an uneconomic level. This invention is more fully illustrated by the following Examples.

EXAMPLE I

Step 1: Preparation of 5-octyl norbornene 1-decene (5984 g) and dicyclopentadiene (770 g, technical grade) were placed in a sealed autoclave and heated to 220° C. for a period of about 3 hours. The reaction mixture was then distilled to give a mixture of exo- and endo-5-octyl-2-norbornene.

Step 2: Preparation of allyl alcohol 5 mole ethylene oxide adducts

To a three gallon stirring autoclave were charged allyl alcohol (1360 g) and potassium hydroxide (4.0 g). After the reaction mixture was purged with nitrogen at 35° C. for a period of 15 minutes, the autoclave was closed and heated to 120° C. Ethylene oxide (5.2 kg) was added incrementally at a temperature range of 120° to 130° C. and a maximum pressure of 60 psig over a period of four and a half hours. The reaction mixture was digested at 125° C. for thirty minutes, cooled to 80° C. and neutralized with 7.0 g of lactic acid. The desired product, allyl alcohol ethoxylates (3.88 kg), was recovered after stripping off lights at 125° C. and 3.0 mm Hg pressure. The product showed 3.55 meq/g of acetylatable hydroxy group, NMR and IR spectra consistent with the desired allyl alcohol ethoxylates.

Step 3: Condensation of allyl alcohol ethoxylates and 5-octyl norbornene

To a 500 ml four neck flask fitted with mechanical stirrer, thermometer, condenser, and nitrogen inlet were charged allyl alcohol ethoxylates (252 g, acetylatable hydroxy group 3.55 meq/g), 5-octyl norbornene (208 g) and boron trifluoride ether complex (6 ml). The reaction mixture was heated with stirring at 115° C. for a period of seven hours under a nitrogen atmosphere. After cooling to room temperature, the reaction mixture was admixed with 250 ml of chloroform and extracted with several 100 ml portions of water until the aqueous extract showed no appreciable gain in volume. From the raffinate was recovered by distillation the unreacted 5-n-octyl norbornene (67 g) as overhead product and α-allyl-ω-(5 and 6-n-octyl norbornyl) polyoxyethylene as bottoms product. Analysis of this product by mercuric acetate addition method showed 2.07 meq/g of unsaturation (theory 2.05 meq/g). The aqueous extracts were combined and extracted with several 100 ml portions of chloroform until the chloroform layer showed no appreciable gain in volume. From the combined chloroform extract was recovered by distillation the unreacted allyl alcohol ethoxylates (102 g). Accordingly, the conversion and the selectivity of the above described reaction were 68% and 99% respectively.

Step 4: Preparation of 5-octyl norbornene ether sulfonate

To 126.5 of the octyl norbornyl-PEG-allyl ether of Step 3 was added 26.0 sodium metabisulfite according to the following procedure: The ether was dissolved in 150 g isopropyl alcohol and 200 g water with 5.1 g 20% sodium hydroxide. Enough 34.3% aqueous solution of sodium metabisulfite was added to lower the pH to 7.1 at 55° C. Thereupon air was bubbled into the solution, and the bisulfite solution added at a rate to maintain pH at 7.2. The addition required 90 minutes, giving 563 g of clear amber solution. Analysis indicated a 79.4% yield of octyl-norbornyl-PEG-propane sulfonate.

The solution was extracted with ethyl acetate to removed unreacted ether, then distilled to remove solvent. The resulting aqueous solution contained 13.9% propane sulfonate.

EXAMPLE II

The condensation of 5-octyl norbornene and allyl alcohol 3.1 molar ethoxylate was carried out and worked up in a manner described in Example I, Step 3. The material was sulfonated in the manner described in Example I, Step 4. Yield of propane sulfonate was 72.8%. Extraction gave a product 22.2% active in aqueous solution. This product is designated Example II product in the Table below.

Utility of the ether propane sulfonate products of Examples I and II in enhanced oil recovery applications was demonstrated by their solubilizing properties for petroleum sulfonates in an oil field brine.

A synthetic brine modeled after Slaughter Field water was prepared using 161 g NaCl, 41.5 g CaCl$_2$, 34.7 g MgCl$_2$:6H$_2$O, 1.0 g Na$_2$SO$_4$ and 0.3 g NaHCO$_3$ in 1000 ml of solution. This concentrate was used in bottle tests at the rate of 4.28 g per 10 g of test solution.

Petroleum sulfonates TRS-18 (oil soluble) and TRS-40 (water soluble), both products of Witco Chemical Co., were blended in a ratio of 3:7 TRS-18:TRS-40. (TRS-18 has an average equivalent weight of 502 and an equivalent weight range of 353 to 640. TRS-40 has an average equivalent weight of 337 and an equivalent weight range of 273 to 440). A 2% solution of the TRS blend was insoluble in Slaughter brine. Addition of 0.5% or 1.0% propane sulfonates (basis total solution) dissolved the precipitate, forming stable solutions. The table summarizes the cloud points (upper stability limits) of the solutions:

TABLE I

| Ether Propane Sulfonate | Cloud Point, °C. | |
|---|---|---|
| | 0.5% | 1.0% |
| Example I, Step 4 Product: ONB-5EO-propane sulfonate | 87° C. | >100° C. |
| Example II Product: ONB-3EO-propane | 28° C. | 66° C. |

TABLE I-continued

| Ether Propane Sulfonate | Cloud Point, °C. | |
|---|---|---|
| | 0.5% | 1.0% |
| sulfonate | | |

All of these four solutions were pearlescent and clear below their cloud points.

EXAMPLE III

Example IIIa.—Preparation of allyl alcohol eight mole ethylene oxide adducts

Allyl alcohol eight mole ethylene oxide adduct was prepared by the ethoxylation of allyl alcohol in the same manner described in Example I. Analyses of the product for unsaturation by mercuric acetate addition method and for acetylatable hydroxy function found 2.42 meq/g and 2.33 meq/g respectively. These values indicated that the products can be described as allyl alcohol 8.1-ethylene oxide adduct. This product is designated Product of Example 3a in the Table below.

Example IIIb.—Preparation of allyl alcohol three mole ethylene oxide adducts

Allyl alcohol three mole ethylene oxide adducts were prepared by ethoxylation of allyl alcohol (707 g) with ethylene oxide (1440 g) in the same manner described in Example I. The resulting product (2036 g) was distilled at 2 mm mercury pressure till pot temperature reached 100° C. in order to remove unreacted allyl alcohol and part of the 3(2-hydroxy ethoxy) propylene product. The bottoms of the distillation, 1741 g, showed 5.20 meq/g of unsaturation and 5.22 meq/g of acetylatable hydroxy function. These values indicated that the products can be described as allyl alcohol 3.1 ethylene oxide adducts. This product is designated Product of Example 3b in the Table below.

Example IIIc.—Condensation of 5-octyl norbornene and allyl alcohol

The condensation of 5-octyl norbornene and allyl alcohol ethoxylates were carried out and worked up in the manner described in Example I, step 3. Results are summarized in Table 2.

TABLE 2

REACTANTS
5-octyl Norbornene CH$_2$=CH$_2$O(CH$_2$CH$_2$O)$_n$H

| | | grams | | | |
|---|---|---|---|---|---|
| Synthesis | grams | n = 8.1[a] | 5[b] | 3.1[c] | Catalyst |
| A | 204 | 429 | — | — | BF$_3$.O(CH$_2$CH$_3$)$_2$ (8 ml) |
| B | 153 | — | 224 | — | Nafion ® 10 g |
| C | 304 | — | — | 300 | BF$_3$.O(CH$_2$CH$_3$)$_2$ (8 ml) |

YIELDS FOR THE PRODUCT

CH$_2$=CHCH$_2$O(CH$_2$CH$_2$O)$_n$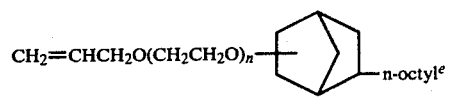n-octyl[e]

| Synthesis | Yield | meq/g unsat.[d] | Conversion, %[f] | Selectivity, %[g] |
|---|---|---|---|---|
| A | 397 g | 1.52 (Theo. 1.50) | 63.7 | 94.4 |
| B | 185 g | 2.00 (Theo. 2.05) | 60.3 | 84.0 |

TABLE 2-continued

| C | 435 g | 2.64 (Theo. 2.51) | 80.0 | 73.4 |

[a]Product of Example IIIa
[b]Product of Example IIIb
[c]Product of Example I, Step 2
[d]By mercuric acetate addition method
[e]Infra red and nuclear magnetic resonance spectra were in excellent agreement with those expected from the desired products.
[f]Basis recovered 5-octyl norbornene
[g]Basis yield and conversion

EXAMPLE IV

In a field in which the primary production has already been exhausted, an injection well is completed in the hydrocarbon-bearing formation and perforations are formed between the interval of 6890–6910 feet. A production well is drilled approximately 415 feet distance from the injection well, and perforations are similarly made in the same hydrocarbon-bearing formation at 6895–6915 feet.

The hydrocarbon-bearing formation in both the injection well and the production well is hydraulically fractured using conventional techniques, and a gravel-sand mixture is injected into the fracture to hold it open and prevent healing of the fracture.

In the next step, oil field brine of 1000 ppm hardness at a temperature of 75° F. containing dissolved therein 1% by weight petroleum sulfonate and 0.5% by weight of the product of Example I, Step 4 is injected via the injection well into the formation at a pressure of about 1300 psig and at the rate of 1.05 barrels per minute. Injection of the driving fluid continues at the rate of 1.05 barrels per minute and at the end of 87 days a substantial production of petroleum is achieved.

What is claimed is:

1. An alkyl norbornyl ether sulfonate of the formula:

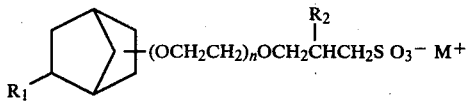

wherein $R_1$ is a substantially linear alkyl group of 4 to 12 carbon atoms; $R_2$ is selected from the group consisting of hydrogen and methyl; M is a cation selected from the group consisting of potassium, sodium and ammonium and n is an integer of from 1 to 12.

2. The alkyl norbornyl ether sulfonate of claim 1 wherein n is an integer of from 3 to 8.

3. The alkyl norbornyl ether sulfonate of claim 1 wherein $R_2$ is hydrogen.

4. The alkyl norbornyl ether sulfonate of claim 1 wherein M is sodium.

5. The alkyl norbornyl ether sulfonate of claim 1 wherein $R_1$ is linear.

6. An aqueous brine solution comprising:
   (a) about 0.1 wgt% to about 2 wgt% of an alkyl norbornyl ether sulfonate of the formula:

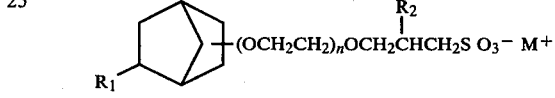

wherein $R_1$ is a substantially linear alkyl group of 4 to 12 carbon atoms; $R_2$ is selected from the group consisting of hydrogen and methyl; M is a cation selected from the group consisting of potassium, sodium and ammonium and n is an integer of from 1 to 12 and;
   (b) about 0.1 weight % to about 4 weight % of a petroleum sulfonate.

7. The solution of claim 6 wherein the petroleum sulfonate has a molecular weight range of about 350 to about 500.

8. The solution of claim 6 wherein n in the alkyl norbornyl ether sulfonate is an integer of from 3 to 8.

* * * * *